(12) United States Patent
Rüttinger et al.

(10) Patent No.: US 9,399,606 B2
(45) Date of Patent: Jul. 26, 2016

(54) CATALYST AND PROCESS FOR THE OXIDATIVE DEHYDROGENATION OF N-BUTENES TO BUTADIENE

(71) Applicant: BASF SE, Luwdigshafen (DE)

(72) Inventors: Wolfgang Rüttinger, Mannheim (DE); Christian Walsdorff, Ludwigshafen (DE); Philipp Grüne, Mannheim (DE)

(73) Assignee: BASF SE, Ludwigshafen (DE)

( * ) Notice: Subject to any disclaimer, the term of this patent is extended or adjusted under 35 U.S.C. 154(b) by 223 days.

(21) Appl. No.: 14/097,375

(22) Filed: Dec. 5, 2013

(65) Prior Publication Data

US 2014/0163288 A1 Jun. 12, 2014

Related U.S. Application Data

(60) Provisional application No. 61/736,568, filed on Dec. 13, 2012, provisional application No. 61/733,927, filed on Dec. 6, 2012.

(51) Int. Cl.

| | |
|---|---|
| *B01J 23/28* | (2006.01) |
| *B01J 23/31* | (2006.01) |
| *B01J 23/34* | (2006.01) |
| *B01J 23/745* | (2006.01) |
| *B01J 23/75* | (2006.01) |
| *B01J 23/881* | (2006.01) |
| *B01J 23/882* | (2006.01) |
| *C07C 5/333* | (2006.01) |
| *C07C 5/42* | (2006.01) |
| *C07C 5/48* | (2006.01) |
| *B01J 23/887* | (2006.01) |
| *B01J 23/889* | (2006.01) |
| *C07C 5/327* | (2006.01) |
| *C10G 27/00* | (2006.01) |
| *C10G 27/04* | (2006.01) |

(52) U.S. Cl.
CPC .............. *C07C 5/48* (2013.01); *B01J 23/8876* (2013.01); *B01J 23/8878* (2013.01); *B01J 23/8898* (2013.01); *C07C 5/327* (2013.01); *C10G 27/00* (2013.01); *C10G 27/04* (2013.01); *C07C 2521/02* (2013.01); *C07C 2521/06* (2013.01); *C07C 2523/04* (2013.01); *C07C 2523/18* (2013.01); *C07C 2523/28* (2013.01); *C07C 2523/34* (2013.01); *C07C 2523/745* (2013.01); *C07C 2523/75* (2013.01); *C07C 2523/887* (2013.01); *C07C 2523/889* (2013.01); *C10G 2300/1081* (2013.01); *C10G 2300/1092* (2013.01); *C10G 2400/20* (2013.01)

(58) Field of Classification Search
CPC ............ B01J 23/28; B01J 23/31; B01J 23/34; B01J 23/745; B01J 23/75; B01J 23/881; B01J 23/882; B01J 23/8878; B01J 23/8892; C07C 5/333; C07C 5/3332; C07C 5/3337; C07C 5/42; C07C 5/321

USPC .................. 502/300, 305, 316, 317, 321, 324; 585/654
See application file for complete search history.

(56) References Cited

U.S. PATENT DOCUMENTS

| | | | |
|---|---|---|---|
| 3,464,930 A | 9/1969 | Friedrichsen et al. | |
| 3,536,775 A | 10/1970 | Hutson et al. | |
| 3,799,886 A | 3/1974 | Felice et al. | |
| 3,907,713 A * | 9/1975 | Grasselli ................. | B01J 21/02 |
| | | | 502/215 |
| 3,911,039 A | 10/1975 | Grasselli et al. | |
| 3,932,551 A | 1/1976 | Grasselli et al. | |
| 3,956,181 A | 5/1976 | Grasselli et al. | |
| 4,162,234 A | 7/1979 | Grasselli et al. | |
| 4,259,211 A | 3/1981 | Krabetz et al. | |
| 4,297,247 A | 10/1981 | Krabetz et al. | |
| 4,305,843 A | 12/1981 | Krabetz et al. | |
| 4,336,409 A | 6/1982 | Yamamoto et al. | |
| 4,397,771 A | 8/1983 | Grasselli et al. | |
| 4,423,281 A | 12/1983 | Yamamoto et al. | |

(Continued)

FOREIGN PATENT DOCUMENTS

| | | |
|---|---|---|
| DE | 734026 C | 4/1943 |
| DE | 1 642 921 A1 | 5/1971 |

(Continued)

OTHER PUBLICATIONS

Jung, J. C., et al., "Catalytic Performance of Bismuth Molybdate Catalysts in the Oxidative Dehydrogenation of $C_4$ Raffinate-3 to 1,3-Butadiene", Applied Catalysis A: General, 2007, vol. 317, pp. 244-249.

(Continued)

*Primary Examiner* — Patricia L Hailey
(74) *Attorney, Agent, or Firm* — Drinker Biddle & Reath LLP

(57) ABSTRACT

The invention relates to a catalyst which comprises a catalytically active multimetal oxide which comprises molybdenum and at least one further metal has the general formula (I)

$$Mo_{12}Bi_aMn_bCo_cFe_dX^1_eX^2_fO_x \quad (I),$$

where the variables have the following meanings:
$X^1$=Si and/or Al;
$X^2$=Li, Na, K, Cs and/or Rb;
a=0.2 to 1;
b=0 to 2;
c=2 to 10;
d=0.5 to 10;
e=0 to 10;
f=0 to 0.5; and
x=is a number determined by the valence and abundance of the elements other than oxygen in (I).

14 Claims, No Drawings

(56) References Cited

U.S. PATENT DOCUMENTS

| | | | |
|---|---|---|---|
| 4,424,141 A | 1/1984 | Grasselli et al. | |
| 4,438,217 A | 3/1984 | Takata et al. | |
| 4,532,365 A * | 7/1985 | Khoobiar | B01J 23/002 568/476 |
| 4,547,615 A | 10/1985 | Yamamoto | |
| 4,621,072 A * | 11/1986 | Arntz | B01J 23/885 427/213 |
| 5,677,261 A | 10/1997 | Tenten et al. | |
| 5,686,373 A * | 11/1997 | Tenten | C07C 51/252 502/312 |
| 5,910,608 A | 6/1999 | Tenten et al. | |
| 5,989,412 A | 11/1999 | Okagami et al. | |
| 6,252,122 B1 * | 6/2001 | Tenten | B01J 23/31 502/244 |
| 6,383,976 B1 | 5/2002 | Arnold et al. | |
| 6,797,839 B1 * | 9/2004 | Hibst | B01J 23/002 502/104 |
| 6,881,702 B2 * | 4/2005 | Arnold | B01J 6/004 502/212 |
| 7,417,173 B2 | 8/2008 | Crone et al. | |
| 2004/0019240 A1 | 1/2004 | Hibst et al. | |
| 2005/0096483 A1 | 5/2005 | Dieterle et al. | |
| 2006/0205978 A1 | 9/2006 | Yunoki et al. | |
| 2007/0167661 A1 | 7/2007 | Johann et al. | |
| 2008/0177105 A1 | 7/2008 | Raichle et al. | |
| 2009/0171117 A1 | 7/2009 | Arnold et al. | |
| 2011/0034330 A1 | 2/2011 | Czaja et al. | |
| 2012/0130137 A1 | 5/2012 | Orita et al. | |
| 2013/0281748 A1 | 10/2013 | Cha et al. | |
| 2014/0163289 A1 | 6/2014 | Grune et al. | |
| 2014/0163290 A1 | 6/2014 | Grune et al. | |
| 2014/0163291 A1 | 6/2014 | Grune et al. | |
| 2014/0163292 A1 | 6/2014 | Grune et al. | |
| 2014/0200379 A1 | 7/2014 | Josch et al. | |
| 2014/0200380 A1 | 7/2014 | Josch et al. | |
| 2014/0200381 A1 | 7/2014 | Josch et al. | |

FOREIGN PATENT DOCUMENTS

| | | |
|---|---|---|
| DE | 2 106 796 A1 | 8/1972 |
| DE | 24 40 329 A1 | 3/1975 |
| DE | 24 47 825 A1 | 8/1975 |
| DE | 25 30 959 A1 | 2/1976 |
| DE | 26 00 128 A1 | 7/1976 |
| DE | 26 26 887 A1 | 12/1977 |
| DE | 29 09 670 A1 | 10/1980 |
| DE | 29 09 671 A1 | 10/1980 |
| DE | 44 42 346 A1 | 5/1996 |
| DE | 100 46 957 A1 | 4/2002 |
| DE | 10 2007 005 606 A1 | 4/2008 |
| DE | 10 2007 004 961 A1 | 7/2008 |
| EP | 0 714 700 A2 | 6/1996 |
| EP | 1 005 908 A2 | 6/2000 |
| EP | 1 382 383 A1 | 1/2004 |
| EP | 2 256 101 A2 | 12/2010 |
| GB | 581902 A | 10/1946 |
| JP | S60-58928 A | 4/1985 |
| JP | 2011/001341 A | 1/2011 |
| JP | 2011/006381 A | 1/2011 |
| KR | 20100028702 A | 3/2010 |
| WO | WO-02/24620 A2 | 3/2002 |
| WO | WO-2005/047226 A1 | 5/2005 |
| WO | WO-2005/063658 A1 | 7/2005 |
| WO | WO-2006/050969 A1 | 5/2006 |
| WO | WO-2006/061202 A1 | 6/2006 |
| WO | WO-2006/091005 A1 | 8/2006 |
| WO | WO-2009/124945 A2 | 10/2009 |
| WO | WO-2010/137595 A1 | 12/2010 |
| WO | WO-2013/002459 A1 | 1/2013 |
| WO | WO-2013/136434 A1 | 9/2013 |

OTHER PUBLICATIONS

Jung, J. C., et al., "Production of 1,3-Butadiene From $C_4$ Raffinate-3 Through Oxidative Dehydrogenation of n-Butene Over Bismuth Molybdate Catalysts", Catal. Surv. Asia, 2009, vol. 13, pp. 78-93.

Alexander, D. S., "Explosions in Butadiene Systems", Industrial and Engineering Chemistry, 1959, vol. 51, No. 6, pp. 733-738.

Zabicky, J., "Analytical and Safety Aspects of Organic Peroxides and Related Functional Groups", in "PATAI's Chemistry of Functional Groups", John Wiley & Sons, Ltd., Chichester, UK, Dec. 2009.

* cited by examiner

CATALYST AND PROCESS FOR THE OXIDATIVE DEHYDROGENATION OF N-BUTENES TO BUTADIENE

CROSS-REFERENCE TO RELATED APPLICATIONS

This application claims benefit (under 35 USC 119(e)) of U.S. Provisional Application No. 61/733,927, filed Dec. 6, 2012, and U.S. Provisional Application No. 61/736,568, filed Dec. 13, 2012, both of which are incorporated by reference.

The invention relates to a catalyst and a process for the oxidative dehydrogenation of n-butenes to butadiene.

Butadiene is an important basic chemical and is used, for example, for the preparation of synthetic rubbers (butadiene homopolymers, styrene-butadiene rubber or nitrile rubber) or for the preparation of thermoplastic terpolymers (acrylonitrile-butadiene-styrene copolymers). Butadiene is also converted into sulfolane, chloroprene and 1,4-hexamethylenediamine (via 1,4-dichlorobutene and adiponitrile). Furthermore, butadiene can be dimerized to produce vinylcyclohexene which can be dehydrogenated to form styrene.

Butadiene can be prepared by thermal cracking (steam cracking) of saturated hydrocarbons, with naphtha usually being used as raw material. The steam cracking of naphtha gives a hydrocarbon mixture of methane, ethane, ethene, acetylene, propane, propene, propyne, allene, butanes, butenes, butadiene, butynes, methylallene, $C_5$-hydrocarbons and higher hydrocarbons.

Butadiene can also be obtained by oxidative dehydrogenation of n-butenes (1-butene and/or 2-butene). Any mixture comprising n-butenes can be used as starting gas mixture for the oxidative dehydrogenation of n-butenes to butadiene. For example, it is possible to use a fraction which comprises n-butenes (1-butene and/or 2-butene) as main constituent and has been obtained from the $C_4$ fraction from a naphtha cracker by removal of butadiene and isobutene. Furthermore, gas mixtures which comprise 1-butene, cis-2-butene, trans-2-butene or mixtures thereof and have been obtained by dimerization of ethylene can also be used as starting gas. In addition gas mixtures which comprise n-butenes and have been obtained by fluid catalytic cracking (FCC) can be used as starting gas.

Gas mixtures which comprise n-butenes and are used as starting gas in the oxidative dehydrogenation of n-butenes to butadiene can also be prepared by nonoxidative dehydrogenation of gas mixtures comprising n-butane.

WO2009/124945 discloses a coated catalyst for the oxidative dehydrogenation of 1-butene and/or 2-butene to butadiene, which can be obtained from a catalyst precursor comprising
(a) a support body,
(b) a shell comprising (i) a catalytically active multimetal oxide which comprises molybdenum and at least one further metal and has the general formula $$Mo_{12}Bi_aCr_bX^1_cFe_dX^2_eX^3_fO_y$$

where
$X^1$=Co and/or Ni,
$X^2$=Si and/or Al,
$X^3$=Li, Na, K, Cs and/or Rb,
$0.2 \leq a \leq 1$,
$0 \leq b \leq 2$,
$2 \leq c \leq 10$,
$0.5 \leq d \leq 10$,
$0 \leq e \leq 10$,
$0 \leq f \leq 0.5$ and y=a number which is determined by the valence and abundance of the elements other than oxygen in order to achieve charge neutrality,
and (ii) at least one pore former.

WO 2010/137595 discloses a multimetal oxide catalyst for the oxidative dehydrogenation of alkenes to dienes, which comprises at least molybdenum, bismuth and cobalt and has the general formula $$Mo_aBi_bCo_cNi_dFe_eX_fY_gZ_hSi_iO_j$$

In this formula X is at least one element selected from the group consisting of magnesium (Mg), calcium (Ca), zinc (Zn), cerium (Ce) and samarium (Sm). Y is at least one element selected from the group consisting of sodium (Na), potassium (K), rubidium (Rb), cesium (Cs) and thallium (Tl). Z is at least one element selected from the group consisting of boron (B), phosphorus (P), arsenic (As) and tungsten (W). a-j are the atom fraction of the respective element, where a=12, b=0.5-7, c=0-10, d=0-10, (where c+d=1-10), e=0.05-3, f=0-2, g=0.04-2, h=0-3 and I=5-48. In the examples, a catalyst having the composition $Mo_{12}Bi_5Co_{2.5}Ni_{2.5}Fe_{0.4}Na_{0.35}B_{0.2}K_{0.08}Si_{24}$ in the form of pellets having a diameter of 5 mm and a height of 4 mm is used in the oxidative dehydrogenation of n-butenes to butadiene.

EP 1 005 908 A2 describes multimetal oxide catalysts for preparing acrolein from propene, which comprise an Ni- and Cr-free mixed metal oxide and can be present in the form of crushed material, shaped bodies or coated catalysts. The multimetal oxide composition has the formula $$Mo_{12}Bi_aX^1_bFe_cX^2_dX^3_eO_y$$

where
X1=Co and/or Ni, preferably Co,
X2=Si and/or Al, preferably Si,
X3=alkali metal, preferably K, Na, Cs and/or Rb, in particular K,
$0.3 \leq a \leq 1$,
$4 \leq b \leq 8$,
$0.5 \leq c \leq 10$,
$0 \leq d \leq 10$,
$0 \leq e \leq 0.5$,
and
y corresponds to the absolute value of the number determined by the valence and stoichiometric coefficients of the remaining elements in order to achieve charge neutrality.

In the case of multimetal oxide catalysts for the oxidative dehydrogenation of alkenes to dienes, there is the problem that they contain toxic or carcinogenic substances and their use in industrial production therefore poses a hazard caused by these poisons. The element chromium is known to have a high toxicity. In particular, oxides of chromium in the oxidation state +VI are to be avoided because of their carcinogenic effect. Although the maximum chromium content of the catalyst disclosed in WO2009/124945 is low, a certain part can be in this oxidation state. A similar situation applies to the catalyst disclosed in WO 2010/137595. Here, nickel oxide is a carcinogenic substance which is to be avoided.

It is an object of the invention to provide a multimetal oxide catalyst for the oxidative dehydrogenation of n-butenes to butadiene, which comprises no chromium as doping element and nevertheless is distinguished by high activity and selectivity.

The object is achieved by a catalyst which comprises a catalytically active multimetal oxide which comprises molybdenum and at least one further metal and has the general formula (I)

$$Mo_{12}Bi_aMn_bCo_cFe_dX^1_eX^2_fO_x \quad (I),$$

where the variables have the following meanings:
X$^1$=Si and/or Al;
X$^2$=Li, Na, K, Cs and/or Rb;
a=0.1 to 5, preferably from 0.3 to 1.5;
b=0 to 2, preferably from 0 to 1;
c=2 to 10, preferably from 3 to 10;
d=0.5 to 10, preferably from 1 to 7;
e=0 to 24, preferably from 0.1 to 2;
f=0 to 1, preferably from 0.01 to 0.5; and
x=is a number determined by the valence and abundance of the elements other than oxygen in (I).

It has been found that replacement of chromium by manganese as doping element leads to a catalyst having comparable activity and selectivity. In contrast to chromium, manganese oxides are not classified as carcinogenic.

In a preferred embodiment, X$^1$ is silicon. In a further preferred embodiment, X$^2$ is potassium.

Particularly preferably,
a=0.5 to 1.4;
b=0.1 to 0.8;
c=5 to 9;
d=2 to 6;
e=1 to 1.9; and
f=0.01 to 0.3.

For example, the multimetal oxide has the formula $Mo_{12}Bi_{0.6}Co_7Fe_3Mn_{0.5}K_{0.08}Si_{1.6}$ or $Mo_{12}Bi_{0.6}Co_7Fe_3Si_{1.6}$.

The catalyst of the invention can be an all-active catalyst or a coated catalyst. If it is a coated catalyst, it has a support body (a) and a shell (b) comprising the catalytically active multimetal oxide which comprises molybdenum and at least one further metal and has the general formula (I).

Support materials suitable for coated catalysts are, for example, porous or preferably nonporous aluminum oxides, silicon dioxide, zirconium dioxide, silicon carbide or silicates such as magnesium silicate or aluminum silicate (e.g. steatite of the grade C 220 from CeramTec). The materials of the support bodies are chemically inert.

The support materials can be porous or nonporous. The support material is preferably nonporous (total volume of the pores based on the volume of the support body preferably ≤1% by volume).

It is particularly possible to use essentially nonporous, spherical supports composed of steatite (e.g. steatite of the type C 220 from CeramTec) which have a rough surface and a diameter of from 1 to 8 mm, preferably from 2 to 6 mm, particularly preferably from 2 to 3 or from 4 to 5 mm. However, the use of cylinders composed of chemically inert support material and having a length of from 2 to 10 mm and an external diameter of from 4 to 10 mm as support bodies is also useful. In the case of rings as support bodies, the wall thickness is usually from 1 to 4 mm. Preferred ring-shaped support bodies have a length of from 2 to 6 mm, an external diameter of from 4 to 8 mm and a wall thickness of from 1 to 2 mm. Rings having the geometry 7 mm×3 mm×4 mm (external diameter×length×internal diameter) are also especially suitable as support bodies. The layer thickness of the shell (b) composed of a multimetal oxide composition comprising molybdenum and at least one further metal is generally from 5 to 1000 µm. Preference is given to from 10 to 800 µm, particularly preferably from 50 to 600 µm and very particularly preferably from 80 to 500 µm.

The coated catalyst is produced by applying a layer composed of the multimetal oxide comprising molybdenum and at least one further metal by means of a binder to the support body and drying and calcining the coated support body.

The production of the coated catalyst generally comprises the steps (i) to (vi):
(i) production of a multimetal oxide precursor composition comprising molybdenum and at least one further metal,
(ii) production of a shaped body from the multimetal oxide precursor composition,
(iii) calcination of the shaped body composed of the multimetal oxide precursor composition to produce a multimetal oxide composition,
(iv) milling of the shaped body to form multimetal oxide particles,
(v) coating of the support body with the metal oxide particles,
(vi) thermal treatment of the coated support body.

The production of an all-active catalyst generally comprises the steps (i) to (iii).

According to the invention, finely divided multimetal oxides comprising molybdenum and at least one further metal which are to be used can in principle be obtained by producing an intimate dry mixture from starting compounds of the elemental constituents of the catalytically active oxide composition and thermally treating the intimate dry mixture at a temperature of from 150 to 650° C.

Production of the Multimetal Oxide Catalyst

To produce the finely divided multimetal oxide compositions (step (O), known starting compounds for the elemental constituents other than oxygen of the desired multimetal oxide composition are used in the respective stoichiometric ratio as starting materials, a very intimate, preferably finely divided dry mixture is produced from these and this dry mixture is then subjected to the thermal treatment (calcination). The sources can either be oxides or compounds which can be converted by heating, at least in the presence of oxygen, into oxides. Apart from the oxides, it is therefore possible to use, in particular, halides, nitrates, formates, oxalates, acetates, carbonates or hydroxides as starting compounds.

Further suitable starting compounds of molybdenum are the oxo compounds thereof (molybdates) or the acids derived from these.

Suitable starting compounds of Bi, Fe and Co are, in particular, the nitrates thereof. Suitable starting compounds of manganese are, in particular, nitrates and acetates.

The intimate mixing of the starting compounds can in principle be carried out in dry form or in the form of aqueous solutions or suspensions.

An aqueous suspension can, for example, be produced by combining a solution comprising at least molybdenum and an aqueous solution comprising the remaining metals. Alkali metals or alkaline earth metals can be present in both solutions. A precipitation is carried out by combining the solutions and this leads to formation of a suspension. The temperature in the precipitation can be greater than room temperature, preferably from 30° C. to 95° C. and particularly preferably from 35° C. to 80° C. The suspension can then be aged at elevated temperature for a particular period of time. The period of time for aging is generally in the range from 0 to 24 hours, preferably from 0 to 12 hours and particularly preferably from 0 to 8 hours. The temperature during aging is generally in the range from 20° C. to 99° C., preferably from 30° C. to 90° C. and particularly preferably from 35° C. to 80° C. The suspension is generally mixed by means of stirring during precipitation and aging. The pH of the mixed solutions or suspension is generally in the range from pH 1 to pH 12, preferably from pH 2 to pH 11 and particularly preferably from pH 3 to pH 10.

Removal of the water produces a solid which represents an intimate mixture of the metal components added. The drying step can generally be carried out by evaporation, spray drying or freeze drying or the like. Drying is preferably carried out by spray drying. For this purpose, the suspension is atomized at elevated temperature by means of a spray head which is generally at a temperature of from 120° C. to 350° C. and the dried product is collected at a temperature of >60° C. The residual moisture content, determined by drying of the spray-dried powder at 120° C., is generally less than 20% by weight, preferably less than 15% by weight and particularly preferably less than 12% by weight.

For the production of all-active catalysts, the spray-dried powder is converted into a shaped body in a further step (step (ii)). Possible shaping aids (lubricants) are, for example, water, boron trifluoride or graphite. Based on the composition to be shaped to give the shaped catalyst precursor body, generally ≤10% by weight, usually ≤6% by weight, frequently ≤4% by weight, of shaping aid is added. The abovementioned added amount is usually >0.5% by weight. A lubricating aid which is preferred is graphite.

The calcination of the shaped catalyst precursor body (step (iii)) is generally carried out at temperatures above 350° C. However, a temperature of 650° C. is normally not exceeded during the course of the thermal treatment. According to the invention, the temperature in the thermal treatment advantageously does not exceed 600° C., preferably does not exceed 550° C. and particularly preferably does not exceed 500° C. Furthermore, the temperature during the thermal treatment of the shaped catalyst precursor body in the process of the invention is preferably above 380° C., advantageously above 400° C., particularly advantageously above 420° C. and very particularly preferably above 440° C. The thermal treatment can also be divided into a plurality of stages over time. For example, it is possible firstly to carry out a thermal treatment at a temperature of from 150 to 350° C., preferably from 220 to 280° C., and subsequently carry out a thermal treatment at a temperature of from 400 to 600° C., preferably from 430 to 550° C. The thermal treatment of the shaped catalyst precursor body normally takes a number of hours (usually more than 5 hours). The total duration of the thermal treatment frequently extends to more than 10 hours. Treatment times of 45 hours or 35 hours are usually not exceeded in the thermal treatment of the shaped catalyst precursor body. The total treatment time is often less than 30 hours. A temperature of 500° C. is preferably not exceeded in the thermal treatment of the shaped catalyst precursor body and the treatment time in the temperature window 400° C. preferably extends to from 5 to 30 hours.

The calcination of the shaped catalyst precursor bodies can be carried out either under inert gas or under an oxidative atmosphere such as air (mixture of inert gas and oxygen) or under a reducing atmosphere (e.g. mixture of inert gas, $NH_3$, CO and/or $H_2$ or methane). It goes without saying that the thermal treatment can also be carried out under reduced pressure. The thermal treatment of the shaped catalyst precursor bodies can in principle be carried out in a wide variety of furnace types, e.g. heatable convection chambers, tray furnaces, rotary tube furnaces, belt calciners or shaft furnaces. The thermal treatment of the shaped catalyst precursor bodies is preferably carried out in a belt calcination apparatus as recommended in DE-A 10046957 and WO 02/24620. The thermal treatment of the shaped catalyst precursor bodies below 350° C. is generally associated with the thermal decomposition of the sources of the elemental constituents of the desired catalyst which are comprised in the shaped catalyst precursor bodies. This decomposition phase frequently occurs during heating to temperatures of <350° C. in the process of the invention.

In order to produce a coated catalyst, the catalytically active oxide composition obtained after calcination is subsequently converted, e.g. by milling, into a finely divided powder (step (iv)) which is then applied with the aid of a liquid binder to the outer surface of the support body (step (v)). The fineness of the catalytically active oxide composition applied to the surface of the support body is of course matched to the desired shell thickness.

Support materials suitable for producing coated catalysts are porous or preferably nonporous aluminum oxides, silicon dioxide, zirconium dioxide, silicon carbide or silicates such as magnesium silicate or aluminum silicate (e.g. steatite of the grade C 220 from CeramTec). The materials of the support body are chemically inert.

The support materials can be porous or nonporous. The support material is preferably nonporous (total volume of the pores, based on the volume of the support body, preferably ≤1% by volume).

Preferred hollow cylinders as support bodies have a length of from 2 to 10 mm and an external diameter of from 4 to 10 mm. In addition, the wall thickness is preferably from 1 to 4 mm.

Particularly preferred ring-shaped support bodies have a length of from 2 to 6 mm, an external diameter of from 4 to 8 mm and a wall thickness of from 1 to 2 mm. An example is rings having the geometry 7 mm×3 mm×4 mm (external diameter×length×internal diameter) as support bodies.

The layer thickness D of a multimetal oxide composition comprising molybdenum and at least one further metal is generally from 5 to 1000 µm. Preference is given to from 10 to 800 µm, particularly preferably from 50 to 600 µm and very particularly preferably from 80 to 500 µm.

The application of the multimetal oxide comprising molybdenum and at least one further metal to the surface of the support body can be carried out in a manner corresponding to the processes described in the prior art, for example as described in US-A 2006/0205978 and EP-A 0 714 700.

In general, the finely divided compositions are applied to the surface of the support body with the aid of a liquid binder. Possible liquid binders are, for example, water, an organic solvent or a solution of an organic substance, (e.g. an organic solvent) in water or in an organic solvent.

A solution comprising from 20 to 95% by weight of water and from 5 to 80% by weight of an organic compound is particularly advantageously used as liquid binder. The organic content of the abovementioned liquid binders is preferably from 10 to 50% by weight and particularly preferably from 10 to 30% by weight.

Preference is generally given to organic binders or binder components whose boiling point or sublimation temperature at atmospheric pressure (1 atm) is ≥100° C., preferably ≥150° C. The boiling point or sublimation point of such organic binders or binder components at atmospheric pressure is very particularly preferably at the same time below the maximum calcination temperature employed during production of the molybdenum-comprising finely divided multimetal oxide. This maximum calcination temperature is usually ≤600° C., frequently ≤500° C.

Organic binders which may be mentioned by way of example are monohydric or polyhydric organic alcohols such as ethylene glycol, 1,4-butanediol, 1,6-hexanediol or glycerol, monobasic or polybasic organic carboxylic acids such as propionic acid, oxalic acid, malonic acid, glutaric acid or maleic acid, amino alcohols such as ethanolamine or diethanolamine and also monofunctional or polyfunctional organic amides such as formamide. Suitable organic binder promoters which are soluble in water, in an organic liquid or in a mixture of water and an organic liquid are, for example, monosaccharides and oligosaccharides such as glucose, fructose, sucrose and/or lactose.

Particularly preferred liquid binders are solutions comprising from 20 to 95% by weight of water and from 5 to 80% by weight of glycerol. The proportion of glycerol in these aqueous solutions is preferably from 5 to 50% by weight and particularly preferably from 8 to 35% by weight.

The application of the molybdenum-comprising finely divided multimetal oxide to the support body (step (v)) can be carried out by dispersing the finely divided composition of molybdenum-comprising multimetal oxide in the liquid binder and spraying the resulting suspension onto agitated and optionally hot support bodies, as described in DE-A 1642921, DE-A 2106796 and DE-A 2626887. After spraying-on is complete, the moisture content of the resulting coated catalyst can, as described in DE-A 2909670, be reduced by passing hot air over the catalysts.

Pore formers such as malonic acid, melamine, nonylphenol ethoxylate, stearic acid, glucose, starch, fumaric acid and succinic acid can be additionally added to the finely divided multimetal oxide applied to the support in order to produce a suitable pore structure of the catalyst and improve its mass transfer properties.

However, the support bodies are preferably firstly moistened with the liquid binder and the finely divided composition of multimetal oxide is subsequently applied to the surface of the support body moistened with binder by rolling the moistened support bodies in the finely divided composition. To achieve the desired layer thickness, the above-described process is preferably repeated a number of times, i.e. the support body bearing the first coat is moistened again and then coated by contact with dry finely divided composition.

To carry out the process on an industrial scale, it is advisable to employ the process disclosed in DE-A 2909671, but preferably using the binders recommended in EP-A 714700. That is to say, the support bodies to be coated are introduced into a preferably inclined (the angle of the inclination is generally from 30 to 90° C.) rotating vessel (e.g. rotating plate or coating drum).

The temperatures which are necessary to bring about removal of the adhesion promoter (step (vi)) are below the maximum calcination temperature for the catalyst, in general from 200° C. to 600° C. The catalyst is preferably heated to from 240° C. to 500° C. and particularly preferably to temperatures in the range from 260° C. to 400° C. The time until the adhesion promoter has been removed can be a number of hours. The catalyst is generally heated to the abovementioned temperature for from 0.5 to 24 hours in order to remove the adhesion promoter. The time is preferably in the range from 1.5 to 8 hours and particularly preferably in the range from 2 to 6 hours. Flow of a gas around the catalyst can accelerate the removal of the adhesion promoter. The gas is preferably air or nitrogen, particularly preferably air. The removal of the adhesion promoter can, for example, be carried out in an oven through which gas flows or in a suitable drying apparatus, for example a belt drier.

Oxidative Dehydrogenation (Oxydehydrogenation, ODH)

In one or more production cycles, oxidative dehydrogenation of n-butenes to butadiene is carried out by a starting gas mixture comprising n-butenes being mixed with an oxygen-comprising gas and optionally an additional inert gas or steam and brought into contact at a temperature of from 220 to 490° C. with the catalyst according to the invention arranged in a fixed catalyst bed in a fixed-bed reactor.

The reaction temperature of the oxydehydrogenation is generally controlled by means of a heat transfer medium which is located around the reaction tubes. As such liquid heat transfer media, it is possible to use, for example, melts of salts such as potassium nitrate, potassium nitrite, sodium nitrite and/or sodium nitrate and also melts of metals such as sodium, mercury and alloys of various metals. However, ionic liquids or heat transfer oils can also be used. The temperature of the heat transfer medium is in the range from 220 to 490° C. and preferably in the range from 300 to 450° C. and particularly preferably in the range from 350 to 420° C.

Owing to the exothermic nature of the reactions which occur, the temperature can be higher than that of the heat transfer medium in particular sections of the interior of the reactor during the reaction and a hot spot is formed. The position and magnitude of the hot spot is determined by the reaction conditions but can also be regulated by the dilution ratio of the catalyst layer or by the passage of mixed gas. The difference between hot spot temperature and the temperature of the heat transfer medium is generally 1-150° C., preferably 10-100° C. and particularly preferably 20-80° C. The temperature at the end of the catalyst bed is generally 0-100° C. above, preferably 0.1-50° C. above, particularly preferably 1-25° C. above, the temperature of the heat transfer medium.

The oxydehydrogenation can be carried out in all fixed-bed reactors known from the prior art, for example in tray ovens, in a fixed-bed tube reactor or a shell-and-tube reactor or in a plate heat exchanger reactor. A shell-and-tube reactor is preferred.

Furthermore, the catalyst bed installed in the reactor can consist of a single zone or 2 or more zones. These zones can consist of a pure catalyst or be diluted with a material which does not react with the starting gas or components of the product gas formed by the reaction. Furthermore, the catalyst zones can consist of all-active catalysts or supported coated catalysts.

As starting gas, it is possible to use pure n-butenes (1-butene and/or cis-/trans-2-butene) but also a gas mixture comprising butenes. Such a mixture can be obtained, for example, by nonoxidative dehydrogenation of n-butane. It is also possible to use a fraction which comprises n-butenes (1-butene and/or 2-butene) as main constituent and has been obtained from the $C_4$ fraction from the cracking of naphtha by removal of butadiene and isobutene. Furthermore, it is also possible to use, as starting gas, gas mixtures which comprise pure 1-butene, cis-2-butene, trans-2-butene or mixtures thereof and have been obtained by dimerization of ethylene. It is also possible to use, as starting gas, gas mixtures which comprise n-butenes and have been obtained by fluid catalytic cracking (FCC).

In an embodiment of the process of the invention, the starting gas mixture comprising n-butenes is obtained by nonoxidative dehydrogenation of n-butane. A high yield of butadiene, based on n-butane used, can be obtained by coupling a nonoxidative catalytic dehydrogenation with the oxidative dehydrogenation of the n-butenes formed. The nonoxidative catalytic dehydrogenation of n-butane gives a gas mixture comprising butadiene, 1-butene, 2-butene and unreacted n-butane and also secondary constituents. Usual secondary constituents are hydrogen, water vapor, nitrogen, CO and $CO_2$, methane, ethane, ethene, propane and propene. The composition of the gas mixture leaving the first dehydrogenation zone can vary greatly depending on the mode of operation of the dehydrogenation. Thus, when the dehydrogenation is carried out with introduction of oxygen and additional hydrogen, the product gas mixture has a comparatively high content of water vapor and carbon oxides. In modes of operation without introduction of oxygen, the product gas mixture from the nonoxidative dehydrogenation has a comparatively high content of hydrogen.

The product gas stream from the nonoxidative dehydrogenation of n-butane typically comprises from 0.1 to 15% by volume of butadiene, from 1 to 15% by volume of 1-butene, from 1 to 25% by volume of 2-butene (cis/trans-2-butene), from 20 to 70% by volume of n-butane, from 1 to 70% by volume of water vapor, from 0 to 10% by volume of low-boiling hydrocarbons (methane, ethane, ethene, propane and propene), from 0.1 to 40% by volume of hydrogen, from 0 to 70% by volume of nitrogen and from 0 to 5% by volume of carbon oxides. The product gas stream from the nonoxidative dehydrogenation can be fed without further work-up to the oxidative dehydrogenation.

Furthermore, any impurities can be present in the starting gas for the oxydehydrogenation in amounts which do not inhibit the effect of the present invention. In the preparation of butadiene from n-butenes (1-butene and cis-/trans-2-butene), impurities which may be mentioned are saturated and unsaturated, branched and unbranched hydrocarbons such as methane, ethane, ethene, acetylene, propane, propene, propyne, n-butane, isobutane, isobutene, n-pentane and also dienes such as 1,2-butadiene. The amounts of impurities are generally 70% or less, preferably 30% or less, more preferably 10% or less and particularly preferably 1% or less. The concentration of linear monoolefins having 4 or more carbon atoms (n-butenes and higher homologs) in the starting gas is not restricted in any particular way; it is generally 35.0-99.99% by volume, preferably 71.0-99.0% by volume and even more preferably 75.0-95.0% by volume.

To carry out the oxidative dehydrogenation at complete conversion of butenes, a gas mixture having a molar oxygen:n-butenes ratio of at least 0.5 is necessary. Preference is given to working at an oxygen:n-butenes ratio of from 0.55 to 10. To set this value, the starting gas can be mixed with oxygen or an oxygen-comprising gas, for example air, and optionally additionally inert gas or steam. The oxygen-comprising gas mixture obtained is then fed to the oxydehydrogenation.

The gas comprising molecular oxygen is a gas which generally comprises more than 10% by volume, preferably more than 15% by volume and even more preferably more than 20% by volume, of molecular oxygen and specifically is preferably air. The upper limit to the content of molecular oxygen is generally 50% by volume or less, preferably 30% by volume or less and even more preferably 25% by volume or less. In addition, any inert gases can be present in amounts which do not inhibit the effect of the present invention in the gas comprising molecular oxygen. As possible inert gases, mention may be made of nitrogen, argon, neon, helium, CO, $CO_2$ and water. The amount of inert gases is in the case of nitrogen generally 90% by volume or less, preferably 85% by volume or less and even more preferably 80% by volume or less. In the case of constituents other than nitrogen, they are generally present in amounts of 10% by volume or less, preferably 1% by volume or less. If this amount becomes too great, it becomes ever more difficult to supply the reaction with the oxygen required.

Furthermore, inert gases such as nitrogen and also water (as water vapor) can be comprised together with the mixed gas composed of starting gas and the gas comprising molecular oxygen. Nitrogen is present for setting the oxygen concentration and for preventing formation of an explosive gas mixture, and the same applies to water vapor. Water vapor is also present in order to control carbonization of the catalyst and to remove the heat of reaction. Water (as water vapor) and nitrogen are preferably mixed into the mixed gas and introduced into the reactor. When water vapor is introduced into the reactor, a proportion of 0.2-5.0 (parts by volume), preferably 0.5-4 and even more preferably 0.8-2.5, based on the introduced amount of the abovementioned starting gas, is preferably introduced. When nitrogen gas is introduced into the reactor, a proportion of 0.1-8.0 (parts by volume), preferably 0.5-5.0 and even more preferably 0.8-3.0, based on the introduced amount of the abovementioned starting gas, is preferably introduced.

The proportion of the starting gas comprising the hydrocarbons in the mixed gas is generally 4.0% by volume or more, preferably 6.0% by volume or more and even more preferably 8.0% by volume or more. On the other hand, the upper limit is 20% by volume or less, preferably 16.0% by volume or less and even more preferably 13.0% by volume or less. In order to safely avoid the formation of explosive gas mixtures, nitrogen gas is firstly introduced into the starting gas or into the gas comprising molecular oxygen before the mixed gas is obtained, the starting gas and the gas comprising molecular oxygen are mixed so as to give the mixed gas and this mixed gas is then preferably introduced.

During stable operation, the residence time in the reactor is not restricted in any particular way in the present invention, but the lower limit is generally 0.3 s or more, preferably 0.7 s or more and even more preferably 1.0 s or more. The upper limit is 5.0 s or less, preferably 3.5 s or less and even more preferably 2.5 s or less. The ratio of throughput of mixed gas to the amount of catalyst in the interior of the reactor is 500-8000 $h^{-1}$, preferably 800-4000 $h^{-1}$ and even more preferably 1200-3500 $h^{-1}$. The space velocity of butenes over the catalyst (expression in $g_{butenes}/(g_{catalyst}*hour)$) in stable operation is generally 0.1-5.0 $h^{-1}$, preferably 0.2-3.0 $h^{-1}$ and even more preferably 0.25-1.0 $h^{-1}$. Volume and mass of the catalyst are based on the complete catalyst consisting of support and active composition.

Regeneration of the Multimetal Oxide Catalyst

In general, a regeneration step is carried out between each two production cycles. The regeneration step is preferably carried out before the decrease in conversion at constant temperature is greater than 25%. The regeneration step is carried out by passing an oxygen-comprising regeneration gas mixture over the fixed catalyst bed at a temperature of from 200 to 450° C., as a result of which the carbon deposited on the multimetal oxide catalyst is burnt off.

The oxygen-comprising regeneration gas mixture used in the regeneration step generally comprises an oxygen-comprising gas and additional inert gases, steam and/or hydrocarbons. In general, it comprises from 0.5 to 22% by volume, preferably from 1 to 20% by volume and in particular from 2 to 18% by volume, of oxygen.

Work-Up of the Product Gas Stream

The product gas stream leaving the oxidative dehydrogenation of the production step comprises butadiene and generally also unreacted n-butane and isobutane, 2-butene and water vapor. As secondary constituents, it generally comprises carbon monoxide, carbon dioxide, oxygen, nitrogen, methane, ethane, ethene, propane and propene, possibly hydrogen and also oxygen-comprising hydrocarbons, known as oxygenates. In general, it comprises only small proportions of 1-butene and isobutene.

The product gas stream leaving the oxidative dehydrogenation can, for example, comprise from 1 to 40% by volume of butadiene, from 20 to 80% by volume of n-butane, from 0 to 5% by volume of isobutane, from 0.5 to 40% by volume of 2-butene, from 0 to 5% by volume of 1-butene, from 0 to 70% by volume of water vapor, from 0 to 10% by volume of low-boiling hydrocarbons (methane, ethane, ethene, propane and propene), from 0 to 40% by volume of hydrogen, from 0 to 30% by volume of oxygen, from 0 to 70% by volume of nitrogen, from 0 to 10% by volume of carbon oxides and from 0 to 10% by volume of oxygenates. Oxygenates can be, for example, formaldehyde, furan, acetic acid, maleic anhydride, formic acid, methacrolein, methacrylic acid, crotonaldehyde, crotonic acid, propionic acid, acrylic acid, methyl vinyl ketone, styrene, benzaldehyde, benzoic acid, phthalic anhydride, fluorenone, anthraquinone and butyraldehyde.

The product gas stream at the reactor outlet has a temperature close to the temperature at the end of the catalyst bed. The product gas stream is then brought to a temperature of 150-400° C., preferably 160-300° C., particularly preferably 170-250° C. It is possible to isolate the line through which the product gas stream flows in order to keep the temperature in the desired range, but use of a heat exchanger is preferred. This heat exchanger system can be of any type as long as the temperature of the product gas can be kept at the desired level by means of this system. As examples of a heat exchanger, mention may be made of helical heat exchangers, plate heat exchangers, double tube heat exchangers, multitube heat exchangers, boiler helical heat exchangers, boiler jacketed heat exchangers, liquid-liquid contact heat exchangers, air heat exchangers, direct contact heat exchangers and also finned tube heat exchangers. Since part of the high-boiling by-products comprised in the product gas can precipitate while the temperature of the product gas is set to the desired temperature, the heat exchanger system should preferably have two or more heat exchangers. In the case of two or more heat exchangers provided being arranged in parallel and divided cooling of the product gas obtained thus being made possible in the heat exchangers, the amount of high-boiling by-products which are deposited in the heat exchangers is decreased and the operating time of the heat exchangers can thus be prolonged. As an alternative to the above-described method, the two or more heat exchangers provided can be arranged in parallel. The product gas is fed to one or more but not all of the heat exchangers and these heat exchangers can be relieved by other heat exchangers after a particular period of operation. In this method, cooling can be continued, part of the heat of reaction can be recovered and, in parallel thereto, the high-boiling by-products deposited in one of the heat exchangers can be removed. As an organic solvent as mentioned above, it is possible to use any, unrestricted, solvent as long as it is able to dissolve the high-boiling by-products, for example an aromatic hydrocarbon solvent such as toluene, xylene, etc., or an alkali aqueous solvent such as an aqueous solution of sodium hydroxide.

If the product gas stream contains more than only small traces of oxygen, a process step for removing residual oxygen from the product gas stream can be carried out. The residual oxygen can interfere insofar as it can cause butadiene peroxide formation in subsequent process steps and can act as initiator for polymerization reactions. Unstabilized 1,3-butadiene can form dangerous butadiene peroxides in the presence of oxygen. The peroxides are viscous liquids. Their density is higher than that of butadiene. Since they are also only sparingly soluble in liquid 1,3-butadiene, they settle out at the bottom of storage containers. Despite their relatively low chemical reactivity, the peroxides are very unstable compounds which can decompose spontaneously at temperatures in the range from 85 to 110° C. A particular danger is the high shock sensitivity of the peroxides which explode with the brisance of an explosive. The risk of polymer formation is present in particular when butadiene is separated off by distillation and can there lead to deposits of polymers (formation of "popcorn") in the columns. The removal of oxygen is preferably carried out immediately after the oxidative dehydrogenation. In general, catalytic combustion stages in which oxygen is reacted in the presence of a catalyst with hydrogen added in this stage is carried out for this purpose. This reduces the oxygen content down to small traces.

The product gas from the $O_2$ removal stage is then brought to an identical temperature level as has been described for the region downstream of the ODH reactor. Cooling of the compressed gas is carried out by means of heat exchangers, which can be configured, for example, as shell-and-tube heat exchangers, helical heat exchangers or plate heat exchangers. The heat removed here is preferably utilized for heat integration in the process.

A major part of the high-boiling secondary components and of the water can subsequently be separated off from the product gas stream by cooling. This separation is preferably carried out in a quench. This quench can comprise one or more stages. Preference is given to using a process in which the product gas is brought into contact directly with the cooling medium and cooled thereby. The cooling medium is not subject to any particular restrictions, but preference is given to using water or an alkaline aqueous solution. This gives a gas stream in which n-butane, 1-butene, 2-butenes, butadiene, possibly oxygen, hydrogen, water vapor and in small amounts methane, ethane, ethene, propane and propene, isobutene, carbon oxides and inert gases remain. Furthermore, traces of high-boiling components which have not been quantitatively separated off in the quench can remain in this product gas stream.

The product gas stream from the quench is subsequently compressed in at least one compression stage and subsequently cooled, as a result of which at least one condensate stream comprising water is condensed out and a gas stream comprising n-butane, 1-butene, 2-butenes, butadiene, possibly hydrogen, water vapor and in small amounts methane, ethane, ethene, propane and propene, isobutene, carbon oxides and inert gases, possibly oxygen and hydrogen remains. The compression can be carried out in one or more stages. Overall, the gas stream is compressed from a pressure in the range from 1.0 to 4.0 bar (absolute) to a pressure in the range from 3.5 to 20 bar (absolute). Each compression stage is followed by a cooling stage in which the gas stream is cooled to a temperature in the range from 15 to 60° C. The condensate stream can thus also comprise a plurality of streams in the case of multistage compression. The condensate stream generally comprises at least 80% by weight, preferably at least 90% by weight, of water and further comprises small amounts of low boilers, C4-hydrocarbons, oxygenates and carbon oxides.

Suitable compressors are, for example, turbocompressors, rotary piston compressors and reciprocating piston compressors. The compressors can be driven by, for example, an electric motor, an expander or a gas turbine or steam turbine. Typical compression ratios (outlet pressure:inlet pressure) per compressor stage are, depending on the construction type, in the range from 1.5 to 3.0. Cooling of the compressed gas is carried out by means of heat exchangers, which can be configured, for example, as shell-and-tube heat exchangers, helical heat exchangers or plate heat exchangers. Coolants used in the heat exchangers are cooling water or heat transfer oils. In addition, preference is given to using air cooling using blowers.

The stream comprising butadiene, butenes, butane, inert gases and possibly carbon oxides, oxygen, hydrogen and low-boiling hydrocarbons (methane, ethane, ethene, propane, propene) and small amounts of oxygenates is fed as starting stream to further processing.

The separation of the low-boiling secondary constituents from the product gas stream can be effected by means of conventional separation processes such as distillation, rectification, membrane processes, absorption or adsorption.

To separate off any hydrogen comprised in the product gas stream, the product gas mixture can, optionally after cooling, for example in a heat exchanger, be passed over a membrane which is permeable only to molecular hydrogen and is generally configured as a tube. The molecular hydrogen which has been separated off in this way can, if necessary, be at least partly used in a hydrogenation or else be passed to another use, for example be used for generating electric energy in fuel cells.

The carbon dioxide comprised in the product gas stream can be separated by means of a $CO_2$ gas scrub. The carbon dioxide gas scrub can be preceded by a separate combustion stage in which carbon monoxide is selectively oxidized to carbon dioxide.

In a preferred embodiment of the process, the incondensable or low-boiling gas constituents such as hydrogen, oxygen, carbon oxides, the low-boiling hydrocarbons (methane, ethane, ethene, propane, propene) and inert gas such as possibly nitrogen are separated off by means of a high-boiling absorption medium in an absorption/desorption cycle, giving a $C_4$ product gas stream which consists essentially of $C_4$-hydrocarbons. In general, the $C_4$ product gas stream comprises at least 80% by volume, preferably at least 90% by volume, particularly preferably at least 95% by volume, of the $C_4$-hydrocarbons, essentially n-butane, 2-butene and butadiene.

For this purpose, the product gas stream is, after prior removal of water, brought into contact with an inert absorption medium in an absorption stage and the $C_4$-hydrocarbons are absorbed in the inert absorption medium, giving absorption medium loaded with $C_4$-hydrocarbons and a tailgas comprising the remaining gas constituents. In a desorption stage, the $C_4$-hydrocarbons are liberated again from the absorption medium.

The absorption stage can be carried out in any suitable absorption column known to those skilled in the art. The absorption can be carried out by simply passing the product gas stream through the absorption medium. However, it can also be carried out in columns or in rotary absorbers. The absorption can be carried out in cocurrent, countercurrent or cross-current. The absorption is preferably carried out in countercurrent. Suitable absorption columns are, for example, tray columns having bubblecap trays, centrifugal trays and/or sieve trays, columns having structured packing, e.g. sheet metal packing having a specific surface area of from 100 to 1000 $m^2/m^3$, e.g. Mellapak® 250 Y, and columns having random packing. However, trickle towers and spray towers, graphite block absorbers, surface absorbers such as thick film absorbers and thin film absorbers and also rotary columns, plate scrubbers, crossed-spray scrubbers and rotary scrubbers are also possible.

In an embodiment, the stream comprising butadiene, butene, butane and/or nitrogen and possibly oxygen, hydrogen and/or carbon dioxide is fed into the lower region of an absorption column. In the upper region of the absorption column, the stream comprising solvent and optionally water is introduced.

Inert absorption media used in the absorption stage are generally high-boiling nonpolar solvents in which the $C_4$-hydrocarbon mixture to be separated off has a significantly greater solubility than do the remaining gas constituents to be separated off. Suitable absorption media are comparatively nonpolar organic solvents, for example aliphatic $C_8$-$C_{18}$-alkanes, or aromatic hydrocarbons such as middle oil fractions from paraffin distillation, toluene or ethers having bulky groups, or mixtures of these solvents; a polar solvent such as 1,2-dimethyl phthalate can be added to these. Further suitable absorption media are esters of benzoic ester and phthalic acid with straight-chain $C_1$-$C_8$-alkanols and also heat transfer oils such as biphenyl and diphenyl ether, chlorinated derivatives thereof and also triarylalkenes. One suitable absorption medium is a mixture of biphenyl and diphenyl ether, preferably having the azeotropic composition, for example the commercially available Diphyl®. This solvent mixture frequently comprises dimethyl phthalate in an amount of from 0.1 to 25% by weight.

Suitable absorption media are octanes, nonanes, decanes, undecanes, dodecanes, tridecanes, tetradecanes, pentadecanes, hexadecanes, heptadecanes and octadecanes or fractions which are obtained from refinery streams and comprise the abovementioned linear alkanes as main components.

In a preferred embodiment, an alkane mixture such as tetradecane (industrial C14-C17 fraction) is used as solvent for the absorption.

At the top of the absorption column, an offgas stream comprising essentially inert gas, carbon oxides, possibly butane, butenes such as 2-butenes and butadiene, possibly oxygen, hydrogen and low-boiling hydrocarbons (for example methane, ethane, ethene, propane, propene) and water vapor is taken off. This stream can partly be fed to the ODH reactor or the $O_2$ removal reactor. This enables, for example, the feedstream to the ODH reactor to be adjusted to the desired $C_4$-hydrocarbon content.

The solvent stream loaded with $C_4$-hydrocarbons is introduced into a desorption column. All column internals known to those skilled in the art are suitable for this purpose. In one process variant, the desorption step is carried out by depressurization and/or heating of the loaded solvent. A preferred process variant is the introduction of stripping steam and/or the introduction of fresh steam into the bottom of the desorber. The solvent which has been depleted in $C_4$-hydrocarbons can be fed as a mixture together with the condensed steam (water) to a phase separation, so that the water is separated from the solvent. All apparatuses known to those skilled in the art are suitable for this purpose. In addition, the use of the water separated off from the solvent for generation of the stripping steam is possible.

Preference is given to using from 70 to 100% by weight of solvent and from 0 to 30% by weight of water, particularly preferably from 80 to 100% by weight of solvent and from 0 to 20% by weight of water, in particular from 85 to 95% by weight of solvent and from 5 to 15% by weight of water. The absorption medium which has been regenerated in the desorption stage is recirculated to the absorption stage.

The separation is generally not quite complete, so that, depending on the type of separation, small amounts or only traces of the further gas constituents, in particular high-boiling hydrocarbons, can be present in the $C_4$ product gas stream. The reduction in volume flow brought about by the separation also reduces the burden on the subsequent process steps.

The $C_4$ product gas stream consisting essentially of n-butane, butenes such as 2-butenes and butadiene generally comprises from 20 to 80% by volume of butadiene, from 20 to 80% by volume of n-butane, from 0 to 10% by volume of 1-butene and from 0 to 50% by volume of 2-butenes, with the total amount adding up to 100% by volume. Furthermore, small amounts of isobutane can be comprised.

The $C_4$ product gas stream can subsequently be separated by extractive distillation into a stream consisting essentially of n-butane and 2-butene and a stream comprising butadiene.

The stream consisting essentially of n-butane and 2-butene can be recirculated in its entirety or partly to the $C_4$ feed to the ODH reactor. Since the butene isomers in this recycle stream consist essentially of 2-butenes and these 2-butenes are generally oxidatively dehydrogenated more slowly to butadiene than is 1-butene, this recycle stream can be subjected to a catalytic isomerization process before introduction into the ODH reactor. In this catalytic process, the isomer distribution corresponding to the isomer distribution present in thermodynamic equilibrium can be set.

The extractive distillation can, for example, be carried out as described in "Erdöl and Kohle-Erdgas-Petrochemie", Volume 34 (8), pages 343 to 346, or "Ullmanns Enzyklopädie der Technischen Chemie", Volume 9, 4$^{th}$ edition 1975, pages 1 to 18. For this purpose, the $C_4$ product gas stream is brought into contact with an extractant, preferably an N-methylpyrrolidone (NMP)/water mixture in an extraction zone. The extraction zone is generally configured in the form of a scrubbing column which comprises trays, random packing elements or ordered packing as internals. This generally has from 30 to 70 theoretical plates so that a sufficiently good separating action is achieved. The scrubbing column preferably has a backwashing zone at the top of the column. This backwashing zone serves to recover the extractant comprised in the gas phase by means of a liquid hydrocarbon runback, for which purpose the overhead fraction is condensed beforehand. The mass ratio of extractant to $C_4$ product gas stream in the feed to the extraction zone is generally from 10:1 to 20:1. The extractive distillation is preferably carried out at a temperature at the bottom in the range from 100 to 250° C., in particular at a temperature in the range from 110 to 210° C., a temperature at the top in the range from 10 to 100° C., in particular in the range from 20 to 70° C., and a pressure in the range from 1 to 15 bar, in particular in the range from 3 to 8 bar. The extractive distillation column preferably has from 5 to 70 theoretical plates.

Suitable extractants are butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formyl-morpholine, N-alkyl-substituted cyclic acid amides (lactams) such as N-alkylpyrrolidones, in particular N-methylpyrrolidone (NMP). Alkyl-substituted lower aliphatic acid amides or N-alkyl-substituted cyclic acid amides are generally used. Dimethylformamide, acetonitrile, furfural and in particular NMP are particularly advantageous.

However, it is also possible to use mixtures of these extractants with one another, e.g. NMP and acetonitrile, mixtures of these extractants with cosolvents and/or tert-butyl ethers, e.g. methyl tert-butyl ether, ethyl tert-butyl ether, propyl tert-butyl ether, n-butyl tert-butyl ether or isobutyl tert-butyl ether. A particularly suitable extractant is NMP, preferably in aqueous solution, preferably with from 0 to 20% by weight of water, particularly preferably with from 7 to 10% by weight of water, in particular with 8.3% by weight of water.

The overhead product stream from the extractive distillation column comprises essentially butane and butenes and small amounts of butadiene and is taken off in gaseous or liquid form. In general, the stream consisting essentially of n-butane and 2-butene comprises from 50 to 100% by volume of the n-butane, from 0 to 50% by volume of 2-butene and from 0 to 3% by volume of further constituents such as isobutane, isobutene, propane, propene and $C_5^+$-hydrocarbons.

At the bottom of the extractive distillation column, a stream comprising the extractant, water, butadiene and small proportions of butenes and butanes is obtained and this is fed to a distillation column. In this, butadiene is obtained at the top or as a side offtake stream. A stream comprising extractant and water is obtained at the bottom of the distillation column, with the composition of the stream comprising extractant and water corresponding to the composition introduced into the extraction. The stream comprising extractant and water is preferably recirculated to the extractive distillation.

The extractant solution is transferred to a desorption zone where the butadiene is desorbed from the extraction solution. The desorption zone can, for example, be configured in the form of a scrubbing column having from 2 to 30, preferably from 5 to 20, theoretical plates and optionally a backwashing zone having, for example, 4 theoretical plates. This backwashing zone serves to recover the extractant comprised in the gas phase by means of a liquid hydrocarbon runback, for which purpose the overhead fraction is condensed beforehand. Ordered packing, trays or random packing are provided as internals. The distillation is preferably carried out at a temperature at the bottom in the range from 100 to 300° C., in particular in the range from 150 to 200° C., and a temperature at the top in the range from 0 to 70° C., in particular in the range from 10 to 50° C. The pressure in the distillation column is preferably in the range from 1 to 10 bar. In general, a lower pressure and/or a higher temperature compared to the extraction zone prevails in the desorption zone.

The desired product stream obtained at the top of the column generally comprises from 90 to 100% by volume of butadiene, from 0 to 10% by volume of 2-butene and from 0 to 10% by volume of n-butane and isobutane. To purify the butadiene further, a further distillation as described in the prior art can be carried out.

The invention is illustrated by the following examples.

EXAMPLES

Catalyst Production

Example 1

Production of an all-Active Catalyst 2 solutions A and B were produced.

Solution A:

3200 g of water were placed in a 10 l stainless steel pot. While stirring by means of an anchor stirrer, 4.8 g of a KOH solution (33% by weight of KOH) were added to the initially charged water. The solution was heated to 60° C. 1066 g of an ammonium heptamolybdate solution (($NH_4$)$_6$$Mo_7O_{24}$*$4H_2O$, 54% by weight of Mo) were then added a little at a time over a period of 10 minutes. The suspension obtained was stirred for another 10 minutes.

Solution B:

1629 g of a cobalt(II) nitrate solution (12.9% by weight of Co) were placed in a 5 l stainless steel pot and heated to 60° C. while stirring (anchor stirrer). 600.9 g of an iron(III) nitrate solution (14.2% by weight of Fe) were then added a little at a time over a period of 10 minutes while maintaining the temperature. The solution formed was stirred for another 10 minutes. 575.3 g of a bismuth nitrate solution (11.1% by weight of Bi) were then added while maintaining the temperature. After stirring for a further 10 minutes, 64.8 g of manganese(II) nitrate were added a little at a time as a solid and the dark red solution formed was stirred for another 10 minutes.

At 60° C., the solution B was pumped into solution A by means of a peristaltic pump over a period of 15 minutes.

During the addition and afterwards, the mixture was stirred by means of a high-speed mixer (Ultra-Turrax). 98.22 g of a silica suspension (Ludox; 49% by weight of SiO2) were then added and the mixture was stirred for another 5 minutes. The suspension obtained was spray dried in a spray dryer from NIRO (spray head No. FOA1, speed of rotation: 25 000 rpm) over a period of 1.5 hours. The temperature of the reservoir was maintained at 60° C. during this. The gas inlet temperature of the spray dryer was 340° C., and the gas outlet temperature was 130° C.

The powder obtained was mixed with 1% by weight of graphite, compacted twice under a pressing pressure of 9 bar and broken up by means of a sieve having a mesh opening of 0.8 mm. The broken up material was once again mixed with 2% by weight of graphite and the mixture was pressed by means of a Kilian S100 tableting press to give 5×3×2 mm (external diameter×length×internal diameter) rings. The catalyst precursor obtained was calcined batchwise (1000 g) in a convection furnace from Heraeus, DE (type K, 750/2 S, internal volume 55 l). The following program was used for this purpose:

heating to 130° C. in 72 min, hold for 72 min
heating to 190° C. in 36 min, hold for 72 min
heating to 220° C. in 36 min, hold for 72 min
heating to 265° C. in 36 min, hold for 72 min
heating to 380° C. in 93 min, hold for 187 min
heating to 430° C. in 93 min, hold for 187 min
heating to 490° C. in 93 min, hold for 467 min After the calcination, the catalyst having the calculated stoichiometry $Mo_{12}Co_7Fe_3Bi_{0.6}K_{0.08}Mn_{0.5}Si_{1.6}O_x$ was obtained.

Example 2

A catalyst is produced as per example B (p. 28) of DE 10 2007 004 961 A1. The catalyst has the stoichiometry $Mo_{12}Co_7Fe_3Bi_{0.6}K_{0.08}Si_{1.6}O_x$.

Example 3 (Comparison)

Two solutions A and B were produced.
Solution A:
3200 g of water were placed in a 10 l stainless steel pot. While stirring by means of an anchor stirrer, 5.2 g of a KOH solution (32% by weight of KOH) were added to the initially charged water. The solution was heated to 60° C. 1066 g of an ammonium heptamolybdate solution $((NH_4)_6Mo_7O_{24}*4H_2O$, 54% by weight of Mo) were then added a little at a time over a period of 10 minutes. The suspension obtained was stirred for another 10 minutes.
Solution B:
1771 g of a cobalt(II) nitrate solution (12.3% by weight of Co) were placed in a 5 l stainless steel pot and heated to 60° C. while stirring (anchor stirrer). 645 g of an iron(III) nitrate solution (13.7% by weight of Fe) were then added a little at a time over a period of 10 minutes while maintaining the temperature. The solution formed was stirred for another 10 minutes. 619 g of a bismuth nitrate solution (10.7% by weight of Bi) were then added while maintaining the temperature. After stirring for a further 10 minutes, 109 g of chromium(III) nitrate were added as solid a little at a time and the resulting dark red solution was stirred for another 10 minutes.

While maintaining the temperature of 60° C., the solution B was pumped into the solution A over a period of 15 minutes by means of a peristaltic pump. During the addition and thereafter, the mixture was stirred by means of a high-speed mixer (Ultra-Turrax). After the addition was complete, the mixture was stirred for another 5 minutes. 93.8 g of an SiO2 suspension (Ludox; SiO2 about 49%, from Grace) were then added and the mixture was stirred for a further 5 minutes.

The suspension obtained was spray dried in a spray dryer from NIRO (spray head No. FOA1, speed of rotation 25 000 rpm) over a period of 1.5 hours. The temperature of the reservoir was maintained at 60° C. during this time. The gas inlet temperature of the spray dryer was 300° C., and the gas outlet temperature was 110° C. The powder obtained had a particle size ($d_{50}$) of less than 40 μm.

The powder obtained was mixed with 1% by weight of graphite, compacted twice under a pressing pressure of 9 bar and broken up through a sieve having a mesh opening of 0.8 mm. The broken up material was once again mixed with 2% by weight of graphite and the mixture was pressed by means of a Kilian S100 tableting press to give 5×3×2 mm (external diameter×length×internal diameter) rings.

The catalyst precursor obtained was calcined batchwise (500 g) in a convection furnace from Heraeus, DE (type K, 750/2S, internal volume 55 l). The following program was used for this purpose:

heating to 130° C. in 72 minutes, hold for 72 minutes
heating to 190° C. in 36 minutes, hold for 72 minutes
heating to 220° C. in 36 minutes, hold for 72 minutes
heating to 265° C. in 36 minutes, hold for 72 minutes
heating to 380° C. in 93 minutes, hold for 187 minutes
heating to 430° C. in 93 minutes, hold for 187 minutes
heating to 490° C. in 93 minutes, hold for 467 minutes After the calcination, the catalyst having the calculated stoichiometry $Mo_{12}Co_7Fe_3Bi_{0.6}K_{0.08}Cr_{0.5}Si_{1.6}O_x$ was obtained.

Dehydrogenation Experiments

Examples 4 to 6

Dehydrogenation experiments were carried out in a screening reactor. The screening reactor was a salt bath reactor having a length of 120 cm and an internal diameter of 14.9 mm and a temperature sensor sheath having an external diameter of 3.17 mm. A multiple thermocouple having 7 measurement points was located in the temperature sensor sheath. The bottom 4 measurement points had a spacing of 10 cm and the uppermost 4 measurement points had a spacing of 5 cm.

Butane and raffinate II or 1-butene were introduced in liquid form at about 10 bar through a coriolis flowmeter, mixed in a static mixer and subsequently depressurized and vaporized in a heated vaporizer section. This gas was then mixed with nitrogen and introduced into a preheater having a steatite bed. Water was introduced in liquid form and vaporized in a stream of air in a heating coil. The air/water vapor mixture was combined with the $N_2$/raffinate II/butane mixture in the lower region of the preheater. The completely mixed feed gas was then fed into the reactor, with an analysis stream being able to be taken off for on-line GC measurement. An analysis stream is likewise taken off from the product gas leaving the reactor and this can be analyzed by on-line GC measurement or the proportion by volume of CO and $CO_2$ can be determined by means of an IR analyzer. A pressure regulating valve which sets the pressure level in the reactor is located downstream of the branch for the analysis line.

A 6 cm long after-bed comprising 16 g of steatite balls having a diameter of 3.5-4.5 mm was placed on the catalyst support grid at the lower end of the screening reactor. 44 g of the catalyst from example 1 were then well mixed with 88 g of steatite rings having the same geometry and introduced into the reactor (146 ml bed volume, 88 cm bed height). The catalyst bed was followed by a 7 cm long preliminary bed comprising 16 g of steatite balls having a diameter of 3.5-4.5 mm.

The reactor was operated using from 100 to 250 standard l/h of a reaction gas having the composition 8% of 1-butene, 2% of butane, 12% of oxygen, 10% of water, 68% of nitrogen at a salt bath temperature of 330° C. for 50 hours. The product gases were analyzed by means of GC. The conversion and selectivity data are shown in tables 1 and 2.

The parameters conversion (X) and selectivity (S) calculated in the examples were determined as follows:

$$X = \frac{\text{mol}(butenes_{in}) - \text{mol}(butenes_{out})}{\text{mol}(butenes_{in})}$$

$$S = \frac{\text{mol}(butadiene_{out}) - \text{mol}(butadiene_{in})}{\text{mol}(butenes_{in}) - \text{mol}(butenes_{out})}$$

where mol($XXX_{in}$) is the molar amount of the component XXX at the reactor inlet, mol($XXX_{out}$) is the molar amount of the component XXX at the reactor outlet and butenes represents the sum of 1-butene, cis-2-butene, trans-2-butene and isobutene.

The catalysts from examples 1 to 3 were used for the reaction of butene to form butadiene in the dehydrogenation reactor. 60 g of the 5×3×2 mm (external diameter×length× internal diameter) rings were mixed with 60 g of steatite rings having the same geometry. They were activated by heating them overnight at 400° C. in a mixture of oxygen, nitrogen and steam (10/80/10). The gas velocity was varied in order to alter the conversion (from 100 standard l/h to 250 standard l/h). The salt bath temperature was regulated so that a maximum conversion of about 95% was achieved. The temperatures at which the conversion was about 90% are shown in table 1.

TABLE 1

Activities of the catalysts tested from examples 1 to 3

| Catalyst | Salt bath temperature |
| --- | --- |
| Mo$_{12}$Bi$_{0.6}$Co$_7$Fe$_3$Mn$_{0.5}$K$_{0.08}$Si$_{1.6}$ (example 1) | 335° C. |
| Mo$_{12}$Bi$_{0.6}$Co$_7$Fe$_3$K$_{0.08}$Si$_{1.6}$ (example 2) | 342° C. |
| Mo$_{12}$Bi$_{0.6}$Co$_7$Fe$_3$Cr$_{0.5}$K$_{0.08}$Si$_{1.6}$ (example 3) | 330° C. |

The conversion and selectivity data are shown in table 2. The selectivities at a conversion of about 90% are compared. At a butene conversion of about 90%, all catalysts have the same selectivity for butadiene within the scatter of the measured values. The catalysts therefore differ only in their activity (see temperatures for 90% conversion in table 1).

TABLE 2

Selectivities of the catalysts tested from examples 1 to 3

| Catalyst | Conversion | Selectivity |
| --- | --- | --- |
| Example 1 | 88% | 77% |
|  | 90% | 77% |
| Example 2 | 88% | 78% |
|  | 91% | 79% |
| Example 3 | 88% | 80% |
|  | 92% | 76% |

The invention claimed is:

1. A catalyst which comprises a catalytically active multimetal oxide which comprises molybdenum and at least one further metal has the general formula (I)

$$\text{Mo}_{12}\text{Bi}_a\text{Mn}_b\text{Co}_c\text{Fe}_d\text{X}^1_e\text{X}^2_f\text{O}_x \quad (I),$$

where the variables have the following meanings:
X$^1$=Si and/or Al;
X$^2$=Li, Na, K, Cs and/or Rb;
a=0.2 to 1;
b≥0 to 2;
c=2 to 10;
d=0.5 to 10;
e=0 to 10;
f=0 to 0.5; and
x=is a number determined by the valence and abundance of the elements other than oxygen in (I).

2. The catalyst according to claim 1, wherein X$^1$ formula (I) is silicon.

3. The catalyst according to claim 1, wherein X$^2$ in formula (I) is potassium.

4. The catalyst according to claim 1, wherein, in formula (I),
a=0.5 to 4;
b=0.1 to 0.8;
c=5 to 9;
d=2 to 6;
e=1 to 1.0; and
f=0.01 to 0.3.

5. The catalyst according to claim 1, which is an all-active catalyst.

6. The catalyst according to claim 1, which is a coated catalyst comprising a support body (a) and a shell (b).

7. The catalyst according to claim 6, wherein the support body is a hollow cylinder having a length of from 2 to 6 mm, an external diameter of from 4 to 8 mm, and a wall thickness of from 1 to 2 mm.

8. The catalyst according to claim 6, wherein the support body is composed of steatite.

9. The catalyst according to claim 6, wherein the shell (b) has a layer thickness D of from 50 to 600 µm.

10. A process for the oxidative dehydrogenation of n-butenes to butadiene, wherein a starting gas mixture comprising n-butenes is mixed with an oxygen-comprising gas and brought into contact with a coated catalyst according of claim 1 arranged in a fixed catalyst bed at a temperature of from 220 to 490° C. in a fixed-bed reactor.

11. The process according to claim 10, wherein the fixed-bed reactor is a fixed-bed tube reactor or fixed-bed shell-and-tube reactor.

12. The process according to claim 10, wherein the starting gas mixture comprising n-butenes is obtained by nonoxidative dehydrogenation of n-butane.

13. The process according to claim 10, wherein the starting gas mixture comprising n-butenes is obtained from the C$_4$ fraction from a naphtha cracker by dimerization of ethylene.

14. The process according to claim 10, wherein the starting gas mixture comprising n-butenes is obtained by fluid catalytic cracking (FCC).

* * * * *